US011571524B2

(12) United States Patent
Pohlmann et al.

(10) Patent No.: US 11,571,524 B2
(45) Date of Patent: Feb. 7, 2023

(54) RESPIRATION-CONTROLLED APPLICATION OF AEROSOL IN POWDER FORM DURING THE ARTIFICIAL RESPIRATION OR SUPPORTED RESPIRATION OF A PATIENT

(71) Applicants: Fraunhofer-Gesellschaft zur Forderung der angewandten Forschung e.V., Munich (DE); MTF MediTech Franken GmbH, Eckental (DE)

(72) Inventors: Gerhard Pohlmann, Meerbeck (DE); Felix Carl Wiegandt, Hannover (DE); Peter Iwatschenko, Eckenthal (DE)

(73) Assignees: FRAUNHOFER-GESELLSCHAFT ZUR FÖRDERUNG DER ANGEWANDTEN FORSCHUNG E.V.; MTF MEDITECH FRANKEN GMBH

( * ) Notice: Subject to any disclaimer, the term of this patent is extended or adjusted under 35 U.S.C. 154(b) by 1065 days.

(21) Appl. No.: 16/316,992

(22) PCT Filed: Jun. 27, 2017

(86) PCT No.: PCT/EP2017/065878
§ 371 (c)(1),
(2) Date: Jan. 10, 2019

(87) PCT Pub. No.: WO2018/010954
PCT Pub. Date: Jan. 18, 2018

(65) Prior Publication Data
US 2019/0247595 A1    Aug. 15, 2019

(30) Foreign Application Priority Data
Jul. 13, 2016    (DE) .................... 10 2016 112 822.8

(51) Int. Cl.
*A61M 11/02*     (2006.01)
*A61M 15/00*    (2006.01)
(Continued)

(52) U.S. Cl.
CPC ............ *A61M 11/02* (2013.01); *A61M 11/00* (2013.01); *A61M 15/00* (2013.01);
(Continued)

(58) Field of Classification Search
CPC ...... A61M 11/02; A61M 11/00; A61M 15/00; A61M 15/0086; A61M 16/0057;
(Continued)

(56) References Cited

U.S. PATENT DOCUMENTS 5,113,855 A * 5/1992 Newhouse ........ A61M 15/0093
128/203.15
6,125,844 A * 10/2000 Samiotes .......... A61M 15/0091
128/200.23
(Continued)

FOREIGN PATENT DOCUMENTS

DE    102008050218    7/2009
JP    2014-028023    2/2014
(Continued)

OTHER PUBLICATIONS

Clinical Foundations No. 14, pp. 1-6, Arzu-Ari: "Aerosol Therapy for Ventilator-Dependent Patients: Devices, Issues, Selection and Technique".; Clinical Foundations No. 14, pp. 7-12, panel discussion, moderator Timm Myers: "Aerosol therapy in spontaneously breathing and mechanically ventilated patient: Description, selection and issues".
(Continued)

*Primary Examiner* — Victoria Murphy
(74) *Attorney, Agent, or Firm* — Sand, Sebolt & Wernow Co., LPA (57) ABSTRACT

A system for respiration-controlled application of aerosol in powder form during artificial respiration or assisted respi-
(Continued)

ration of a patient including an interface contacting the patient's respiratory tract, a unit for generating a respiratory gas flow, at least one inspiration line through gas flow is conducted to the interface, an aerosol generator, at least one aerosol line through which the generated aerosol is conducted from the aerosol generator to the interface, and a respiration sensor that detects the patient's respiration signal. A valve in the at least one aerosol line is controlled based on the detected respiratory signal. An intermediate store for generated aerosol in powder form is arranged between the valve and the aerosol generator. The gas flow has a first pressure that is higher than or equal to ambient pressure and the aerosol has a second pressure that is higher than or equal to the first pressure.

13 Claims, 5 Drawing Sheets

(51) Int. Cl.
| | | |
|---|---|---|
| *A61M 16/00* | (2006.01) | |
| *A61M 16/16* | (2006.01) | |
| *A61M 16/10* | (2006.01) | |
| *A61M 16/20* | (2006.01) | |
| *A61M 11/00* | (2006.01) | |
| *A61M 16/14* | (2006.01) | |

(52) U.S. Cl.
CPC .... *A61M 15/0086* (2013.01); *A61M 16/0057* (2013.01); *A61M 16/1065* (2014.02); *A61M 16/14* (2013.01); *A61M 16/16* (2013.01); *A61M 16/206* (2014.02); *A61M 2016/0018* (2013.01); *A61M 2016/0027* (2013.01); *A61M 2202/064* (2013.01); *A61M 2205/3331* (2013.01); *A61M 2205/50* (2013.01); *A61M 2205/7545* (2013.01)

(58) Field of Classification Search
CPC .. A61M 16/1065; A61M 16/14; A61M 16/16; A61M 16/206; A61M 2016/0018; A61M 2016/0027; A61M 2202/064; A61M 2205/3331; A61M 2205/50; A61M 2205/7545

See application file for complete search history.

(56) References Cited

U.S. PATENT DOCUMENTS

| | | |
|---|---|---|
| 2005/0229926 A1 | 10/2005 | Fink et al. |
| 2007/0295328 A1* | 12/2007 | Raghuprasad .... A61M 15/0016 128/200.14 |
| 2009/0266363 A1 | 10/2009 | Clemensen et al. |
| 2011/0108025 A1* | 5/2011 | Fink ................... A61M 11/005 128/200.23 |

FOREIGN PATENT DOCUMENTS

| | | | |
|---|---|---|---|
| WO | 2005048982 | 6/2005 | |
| WO | 2006108558 | 10/2006 | |
| WO | WO-2006108558 A1 * | 10/2006 | ............ A61M 11/06 |
| WO | 2009042187 | 4/2009 | |
| WO | 2010122103 | 10/2010 | |
| WO | 2011/004275 | 1/2011 | |

OTHER PUBLICATIONS

Walsh, B. K., et al., "Perinatal and pediatric respiratory care, evolve learning system", 3rd edition, ISBN 978-1-4160-2448-4 and/or Philip Chi Lip Kwok, Hak-Kim Chan, "Delivery of inhalation drugs to children for asthma and other respiratory diseases", Advanced Drug Delivery Reviews 73 (2014), pp. 83-88.

* cited by examiner

RESPIRATION-CONTROLLED APPLICATION OF AEROSOL IN POWDER FORM DURING THE ARTIFICIAL RESPIRATION OR SUPPORTED RESPIRATION OF A PATIENT

TECHNICAL FIELD

The present invention relates to a system for respiration-controlled application of an aerosol in powder form during artificial respiration or supported respiration of a patient and a corresponding method. It also relates to a valve for use in the system according to the invention.

BACKGROUND

Background Information

Artificial respiration is understood to refer to partial or complete takeover of physiological respiration by external aids or sources. This is done when spontaneous respiration is inadequate or fails completely. Supported respiration, however, refers to assistance for spontaneous respiration, in which a continuous excess pressure (CPAP, continuous positive airway pressure) is applied throughout an entire respiratory cycle. The patient here can determine the depth and frequency of respiration as well as the air flow rate himself. The prerequisite for using supported respiration is thus the patient's fundamental ability to participate in his own respiration.

Thus, for example, there is a great medical need for such systems and methods in local treatment of lung infections (bacterial, viral or mycotic) with active ingredients, in particular in patients receiving artificial respiration or supported respiration. This need exists in particular in treatment of so-called respiratory distress syndrome (IRDS) in premature and neonatal infants in which the infant's immature lungs fail to produce enough of the so-called surfactant (a special surface-active substance in the lungs). Alveoli therefore collapse and then cannot participate in the gas exchange. Oxygen deficiency, dyspnea and possibly even lung damage are the consequences. To avoid IRDS often a surfactant must be introduced into the lungs when a premature or newborn infant receive artificial respiration or supported respiration. At present, this is accomplished invasively by installation of a surfactant suspension.

The local pulmonary demand for active ingredient for inhalative administration of up to a few 100 mg per day is thus two to three orders of magnitude greater than that in common inhalative administration. There is an urgent demand for further development of portable and stationary inhalation equipment to be used by patients and also in particular in the development of aerosol delivery methods to be combined with intensive care respiration technologies.

Shortening application times by using higher dose rates at the patient interface is a high medical demand in chronic diseases in particular. Dispersion of powders is a promising option, but it is important to optimally combine aerosol technology with respiration technology here.

For children in particular, the lack of coordination ability as well as the changing pulmonary anatomy and respiratory mechanics, which change over the course of child development, require systems that can adapt in an automated manner to the individual givens. Therefore, a close association between sensory in situ respiration monitoring and control of the dose to be administered is necessary. In general, respiration-triggered nebulization of liquids is already in widespread use (Clinical Foundations No. 14, pp. 1-6, Arzu Ari: "Aerosol Therapy for Ventilator-Dependent Patients: Devices, Issues, Selection and Technique"; Clinical Foundations No. 14, pp. 7-12, panel discussion, moderator Timm Myers: "Aerosol therapy in spontaneously breathing and mechanically ventilated patient: Description, selection and issues").

However, powder inhalers have also been described to an increasing extent. Thus, WO 2010/122 103 A1, for example, discloses a system for administering an aerosol in powder form in an artificial respiration system, wherein the aerosol in powder form is dosed continuously. With this type of dosing, however, a greater amount of the powdered aerosol is consumed without being deposited in the deep areas of the lungs, where it can manifest its full effect. Such a mode of operation is therefore expensive and inefficient.

SUMMARY

The object of the invention is therefore to modify a system for respiration-controlled administration of an aerosol in powder form, such that the therapeutic efficiency is increased while a simple and inexpensive design is possible at the same time.

This object is achieved by a system for respiration-controlled administration of an aerosol in powder form in artificial respiration or assisted respiration of a patient, having the features of an interface which can be brought into contact with the respiratory tract of the patient to receive artificial respiration or supporting respiration, a device for producing a respiration gas stream wherein the respiratory gas stream has a first pressure which is greater than or equal to the ambient pressure, at least one inspiration line through which the respiratory gas stream is sent to the interface, an aerosol generator, at least one aerosol line through which the powdered aerosol produced is sent from the aerosol generator to the interface and a respiration sensor which detects the patient's respiration signal to receive artificial respiration or supporting respiration, characterized in that a valve is arranged in the at least one aerosol line between the interface and the aerosol generator, the valve being controlled as a function of the respiratory signal detected, and a temporary storage device for storing powdered aerosol thereby produced is arranged between the valve and the aerosol generator, wherein the powdered aerosol stored in the temporary storage device has a second pressure which is greater than or equal to the first pressure. Advantageous refinements of such a system are that the valve, when open, has an aperture which corresponding to the cross section of the at least one aerosol line. The valve also has a switching time of less than 20 ms. The line volume between the valve and the interface is less than the patient's tidal volume. Furthermore, the line volume between the valve and the interface amounts to max. 1/10 of the patient's tidal volume. The sum of the volume of the temporary storage device and of the line volume between the temporary storage device and the valve is greater than the patient's tidal volume. The sum of the volume of the temporary storage device and of the line volume between the temporary storage device and the valve amounts to at least twice the patient's tidal volume. Additionally, the temporary storage device has at least one elastic wall. The aerosol generator is controlled as a function of the second pressure prevailing in the temporary storage device. An additional aspect of the invention is presented by a valve for use in the system according to the invention for respiration-controlled administration of an aerosol in a powder form in artificial respiration or assisted respiration of a patient, having the features of a channel with connecting elements and a plurality of closure elements, wherein the closure elements have flexible wall segments and are arranged on the inside wall of the channel along a circumferential section in a radially uniform distribution so that the flexible wall segments each form control chambers with the inside wall of the channel with the inside wall of the channel, these control chambers being interconnected with one another to form an overall volume system and being acted upon with control fluid so that the closure elements are squeezed into the cross section of the channel and with respect to one another because of the increase in pressure of the control fluid in the control chambers. Advantageous refinements of such a valve are that the valve has three, four, or five identical closure elements in a radially symmetrical distribution, wherein the volume of the control chambers of the closure elements is the same. The total volume system has a total volume amounting to maximum of ⅓ of the patient's tidal volume. Another aspect of the present invention is formed by a method for respiration-controlled administration of an aerosol in powder form in artificial respiration or assisted respiration of a patient, having the features of generating a respiratory gas stream, which has a first pressure greater than or equal to ambient pressure, sending the respiratory gas stream to an interface which is in contact with the respiratory tract of a patient to receive artificial respiration or supporting respiration, producing powdered aerosol, sending the powdered aerosol thereby produced to the interface, detecting a respiratory signal, characterized in that the powdered aerosol thereby produced is stored in a temporary storage device between the site of production of the powdered aerosol and the interface, wherein the powdered aerosol stored in the temporary storage device has a second pressure which is greater than or equal to the first pressure and addition of the powdered aerosol thereby produced is regulated by a valve as a function of the detected respiratory signal, the valve being situated between the temporary storage device and the interface.

The present invention is therefore directed at respiration-controlled administration of an aerosol in powder form in a circulation system for administering respiratory gas, in particular in assisted respiration by CPAP but also in artificial respiration. The invention is for use in premature and newborn infants in particular as well as small children, but also preteens and adults, for example, those with chronic obstructive pulmonary disease (COPD).

In a corresponding system having an interface that can be brought into contact with the respiratory tract of the patient to receive artificial respiration or assisted respiration, a device for generating a respiratory gas stream, wherein the respiratory gas stream has a first pressure, which is greater than or equal to the ambient pressure, at least one inspiration line through which the respiratory gas stream is conveyed to the interface, an aerosol generating device, at least one aerosol line through which the resulting aerosol in powder form is conveyed to the interface and a respiration sensor that detects the patient's respiration signal, the approach according to the invention consists of keeping the aerosol in powder form on hand directly at the interface prior to administration and supplying it as needed. The supply is regulated by a valve arranged in at least one aerosol line between the interface and the aerosol generator. To do so, the valve is controlled as a function of the detected respiratory signal, and the resulting aerosol in powder form is kept on hand in a temporary storage device situated between the valve and the aerosol generator, wherein the aerosol in powder form kept on hand in the intermediate storage device has a second pressure, which is greater than or equal to the first pressure, in particular optionally being 2-3 mbar greater. The aerosol in powder form is thus added directly to or even completely replaces the respiration gas stream for a short period of time when the valve is opened.

The term "aerosol in powder form" refers to a heterogeneous mixture (dispersion) of solid suspended particles in a gas. The solid suspended particles result from an inhalable dry powder that can be administered dry as well as being moistened prior to administration in order to ensure that inhalable dry powders having hygroscopic properties in particular do not dry out the lungs. The aerosol in powder form may then have a maximum particle diameter of 4 μm in particular.

The respiration signal may be comprised of inhalation, exhalation and pause phases. In artificial respiration, the machine respiration strokes are administered either by volume control (volume controlled ventilation, VCV) or by pressure control (pressure controlled ventilation PCV) in accordance with the target variable. The respiration sensor can determine the respiration signal on the basis of the movement of the rib cage/abdominal wall, the temperature at the interface, the flow at the interface and/or the pressure at the interface. In artificial respiration, the respiration signal can also be detected by the device for producing a respiration gas stream. In this case, the device for producing a respiration gas stream may include the respiration sensor.

For control of the valve, the detected respiration signal of the respiration sensor is evaluated and the course of the respiratory cycle is determined. Then the valve is opened at a predetermined point in time within the respiratory cycle, during which the aerosol in powder form is to be administered.

A device for producing a respiration gas stream here may comprise a fan, a pressurized gas bottle or the like.

An aerosol-generating device may comprise a device according to WO 2010/122 103 A1, for example.

The aerosol in powder form produced in this way can be sent directly to the interface via the at least one aerosol line as well as being sent indirectly via the at least one inspiration line, wherein the aerosol in powder form thereby produced is sent through the at least one aerosol line to the at least one inspiration line, in which it is further conveyed to the interface.

An interface may be a respiration mask, a tube, a mouthpiece, a nasal cannula, a prong or the like. The interface here may comprise a connection for the at least one inspiration line. In addition, the interface may have a connection for the at least one aerosol line and/or a connection for an expiration line.

The expiration line may convey the patient's expiration air stream back to the device for producing a respiratory gas stream, for example. In doing so, the expiration line may have one or more filters to separate the powder particles of the aerosol in powder form contained in the expiration air stream, so that the particles do not penetrate into the device for producing a respiratory gas stream and have a negative effect on its function.

The interface may have another line for a separate removal of the respiratory air containing the aerosol in powder form, wherein this additional line may have an outlet valve. In particular the outlet valve may be controlled as a function of the respiration signal detected by the Orespiration signal so that the (inspiration) valve is opened during inspiration by the patient and the outlet valve is closed and the (inspiration) valve is closed during expiration by the patient and the outlet valve is opened. The dead volume within the interface, i.e., the volume of the expiration air still remaining in the interface after expiration by the patient can be further minimized in this way. It is advantageous here if the outlet valve is connected directly to the interface. In particular the outlet valve may have the same design and the same functioning as the valve. The at least one inspiration line may additionally have one or more filters and/or valves, nonreturn valves or the like between the device for producing the respiratory gas stream, the interface and/or the location where the powdered aerosol thereby produced is added.

It is also advantageous if the valve is located directly at the interface or directly in the area thereof and is small enough not to have a negative effect on the function of the interface, i.e., the operability and positioning of the interface on the patient must not be affected by the size and weight of the valve. At the same time, however, the valve should allow the powdered aerosol thereby produced to pass through optimally when the valve is opened. Therefore, when open, the valve may have an aperture corresponding to the cross section of the at least one aerosol line. It is also advantageous if the valve does not have abrupt transitions such as edges.

In addition, the valve may have a switching time of less than 20 ms in order to implement an optimum dosing time for the powdered aerosol.

To further reduce dead times and/or dead volumes between the aerosol generating device and the interface, the line volume between the valve and interface may be smaller than the patient's tidal volume, in particular the line volume between the valve and interface should amount to max. $\frac{1}{10}$ of the patient's tidal volume.

The term "dead volume" here refers to the volume to be filled first with the powdered aerosol after opening the valve until it reaches the interface. "Dead time" denotes the period of time after which the powdered aerosol reaches the interface after opening the valve.

The following guideline values are definitive for the tidal volume and/or the respiratory rate (source: Walsh, B. K. et al., "Perinatal and pediatric respiratory care, evolve learning system," $3^{rd}$ edition, ISBN 978-1-4160-2448-4 and/or Philip Chi Lip Kwok, Hak-Kim Chan, "Delivery of inhalation drugs to children for asthma and other respiratory diseases," Advanced Drug Delivery Reviews 73 (2014), pp. 83-88):

| | Age classification | Tidal volume (mL/kg) | Respiratory rate (breaths/minute) |
|---|---|---|---|
| Adult | ≥12 years | 7-10 | 12-20 |
| Preteen | 6-12 years | 7-10 | 18-25 |
| Child | 2-6 years | 6-9 | 20-30 |
| Toddler | 1 month-2 years | 5-8 | 20-35 |
| Newborn | 0-30 days | 5-8 | 25-40 |
| Premature | gestation age <38 | 4-6 | 25-60 |

To always provide an adequate amount of powdered aerosol, the sum of the volume of the temporary storage device and the line volume between the temporary storage device and the valve may be greater than the patient's tidal volume, in particular the sum of the volume of the temporary storage device and the volume of the line between the temporary storage device and the valve should amount to at least twice the patient's tidal volume.

In addition, it is advantageous if the temporary storage device has at least one elastic wall to thereby ensure a uniform feed stream of the powdered aerosol over the entire opening period of the valve by means of a constant pressure of the powdered aerosol supplied in the temporary storage device.

To always achieve an adequate supply of powdered aerosol in the temporary storage device, the aerosol generator may be controlled as a function of the second pressure prevailing in the temporary storage device.

In an advantageous refinement, the valve may comprise a channel having connection elements and a plurality of closure elements, wherein the closure elements have flexible wall segments and are arranged, so that they are distributed in a radially uniform manner on the inside wall of the channel along a circumferential section, so that these wall segments form control chambers with the inside wall of the channel, such that the control chambers are interconnected to form an entire volume system, and they can be acted upon by a control fluid, so that the closure elements are squeezed into the cross section of the channel and against one another due to an increase in pressure in the control fluid in the control chambers.

In particular, the valve may comprise three, four or five identical closure elements in a radially symmetrical distribution, wherein the volume of the control chambers of the closure elements is the same. Therefore, the flexible wall segments undergo jaw-shaped deformation due to the increase in pressure of the control fluid and thereby block the aerosol line. Due to the division of the control chamber into a plurality of closure elements, in particular three, four or five closure elements, each being of the same size, based on volume, a particularly great symmetry can be achieved in the valve while closed.

It is additionally advantageous if the closure segments are designed as elastomer membrane-tubular cuffs arranged in the channel, both of whose ends are secured in a pressure-tight manner, such that the elastomer membrane-tubular cuff has a plurality of reinforcements distributed uniformly over the circumference along the length, and the flexible wall segments are formed between the reinforcements, thus forming a plurality of control chambers between the inside wall of the channel and the outside wall of the elastomer membrane-tubular cuff. In particular three, four or five identical control chambers may be formed between the inside wall of the channel and the outside wall of the elastomer membrane-tubular cuff in a radially symmetrical distribution, such that the volume of the control chambers is the same size. In particular the elastomer membrane-tubular cuff may be designed as a silicone membrane-tubular cuff.

In a particularly advantageous variant, the total volume system may have a total volume amounting to max. $\frac{1}{3}$ of the patient's tidal volume in order to be able to ensure that in the event of rupture of the flexible wall segments, only a very small volume of the control fluid will enter the aerosol line and thus the respiratory tract of the patient to receive artificial respiration or supporting respiration. In particular the total volume may amount to max. 0.7 mL if the patient is a premature infant. In this case the valve may have an inside diameter of 5 mm and a length of 10 mm. If the patient is an adult, the total volume may amount to max. 14 mL. The valve here may have an inside diameter of 19 mm and a length of 50 mm. In particular the total volume system may be closed by a movable piston or a flexible element, such that the pressure in the total volume system acted upon by the control fluid is increased by the movement of the piston or the compression of the flexible element.

A valve having the properties (optional) described above is also disclosed as a valve for use in a system for respiration controlled administration of powdered aerosol in artificial respiration or supported respiration of a patient and may constitute an independent aspect of the invention. Since the valve comes in direct contact with the patient, the valve may be designed as a disposable item, which is discarded after use in particular.

In another aspect of the invention, a method for respiration controlled administration of powdered aerosol in artificial respiration or supporting respiration of a patient may be made available. This includes the following steps: producing a respiratory gas stream having a first pressure, which is greater than or equal to ambient pressure; conveying the respiratory gas stream to an interface, which is in contact with the respiratory tract of a patient that is to receive artificial respiration or supporting respiration; producing powdered aerosol; conveying the powdered aerosol to the interface; detecting a respiratory signal, wherein the powdered aerosol thereby produced is stored in a temporary storage device between the interface and the site of production of the powdered aerosol, wherein the powdered aerosol stored in the temporary storage device has a second pressure greater than or equal to the first pressure, in particular 2-3 mbar greater, and wherein the addition of powdered aerosol thereby generated is regulated by a valve situated between the temporary storage device and the interface as a function of the detected respiration signal.

Dosing of the powdered aerosol can be adjusted in the system and/or method according to the invention by means of the addition time and the concentration of powdered aerosol stored in the temporary storage device. In addition, the site of action of the powdered aerosol, i.e., the area of the lungs into which the powdered aerosol will reach, can be adjusted on the basis of the time of addition. Thus, the powdered aerosol will reach the deep areas of the lungs when added directly at the start of the breathing cycle, i.e., at the start of inspiration. In particular the powdered aerosol may be administered as a bolus within with the respiratory cycle.

The system/method according to the invention can also be used possible in artificial respiration and/or supporting respiration using a respiration gas with an elevated oxygen level.

Thus, both the system and the method according to the invention permit optimum dosing of the powdered aerosol and therefore a high therapeutic efficiency, so that the required dosing times or doses of the medication can be reduced. For example, it is possible to estimate that the amount of substance administered to an IRDS patient can be reduced by approx. 60%.

BRIEF DESCRIPTION OF THE SEVERAL VIEWS OF THE DRAWINGS

Additional advantages and features of the invention are derived from the following description of several embodiments on the basis of the accompanying figures, in which.

DETAILED DESCRIPTION

Figure 1:
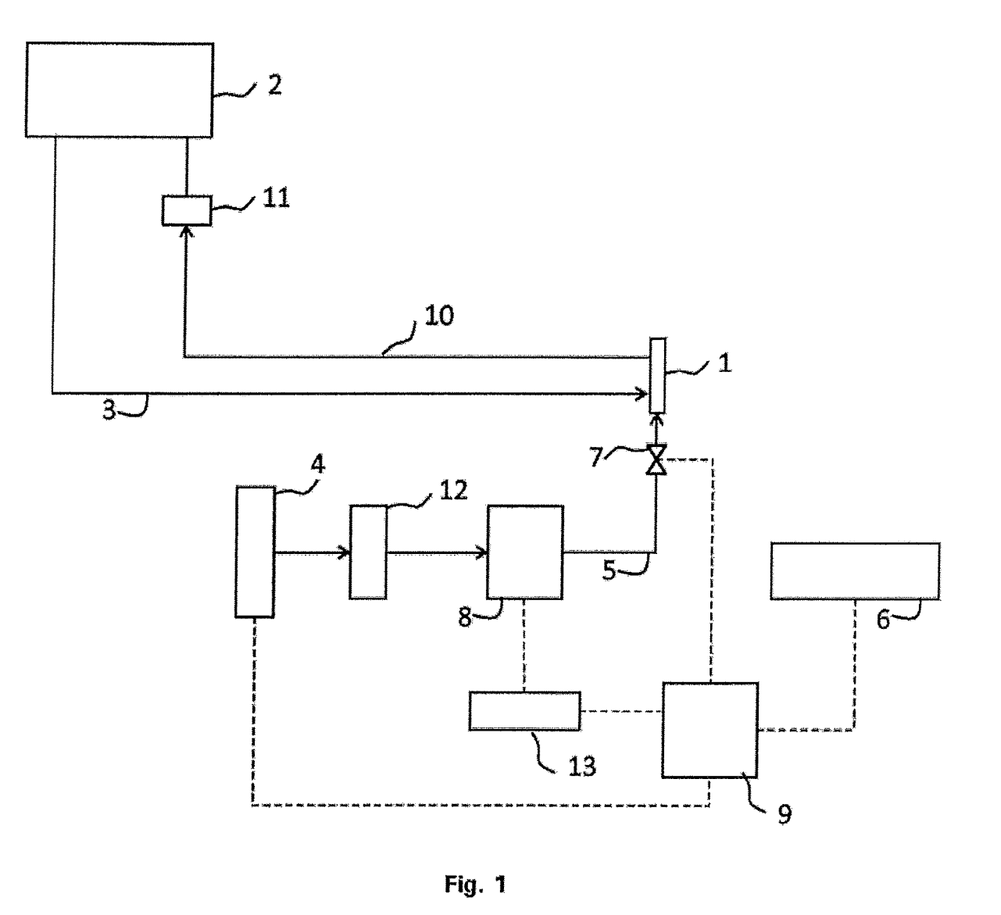
FIG. 1 shows a schematic diagram of the system according to the invention for respiration-controlled administration of powdered aerosol in supporting respiration of a patient (CPAP method)

FIG. 1 illustrates various components of the system according to the invention: an interface 1, which is in contact with the respiratory tract of the patient receiving respiratory support, a device for producing a respiratory gas stream 2, an inspiration line 3, through which the respiration gas stream is sent to the interface 1, an aerosol generator 4, an aerosol line 5, through which the resulting powdered aerosol is sent to the interface 1, a respiration sensor 6, a valve 7 as well as a temporary storage device 8 for storing the powdered aerosol thereby produced, a moistener 12 for moistening the powdered aerosol, a controller 9 for controlling the valve and the aerosol generator, a pressure sensor 13 for detecting the pressure prevailing in the temporary storage device as well as an expiration line 10 having a filter 11.

The device for producing the respiratory gas stream 2 supplies a respiratory gas stream via the inspiration line 3 to the interface 1. The powdered aerosol produced in the aerosol generator 4 is optionally moistened in the moistener 12 and sent through the aerosol line 5 to the interface 1. The valve 7 is in the aerosol line 5 between the temporary storage device 8 and the interface 1 and is controlled by the controller 9 which evaluates the detected respiration signal of the respiration sensor 6. Control of the aerosol generator 3 takes place, for example, as a function of the prevailing pressure 13 of the powdered aerosol in the temporary storage device 8. The expiration air stream of the patient is sent via the expiration line 10 to the device for producing a respiratory gas stream 2, wherein the powder particles of the powdered aerosol contained in the expiration air stream are separated first in the filter 11, so that they do not have a negative effect on the function of the device for producing the respiratory gas stream 2.

The powdered aerosol is produced in the aerosol generator 4 until the pressure prevailing in the temporary storage device 8 corresponds to the pressure predetermined by the controller 9. The valve 7 is closed. The patient receives continuous supporting respiration through a respiratory gas stream supplied by the device for producing a respiratory gas stream 2. The respiration sensor 6 detects the respiration signal of the patient and sends it on to the controller 9, which evaluates it. At a predetermined point in time within the respiratory cycle, during which the powdered aerosol is to be dosed, the valve 7 is opened on the basis of a corresponding signal of the controller 9, and the powdered aerosol is thereby mixed directly with the respiratory gas stream, or the powdered aerosol may even replace it for a brief period of time. After the end of the preset addition time, the valve 7 is closed again by a signal from the controller 9. In doing so, the switching time of the valve amounts to less than 20 ms in order to be able to implement in optimum dosing time.

Figure 2:
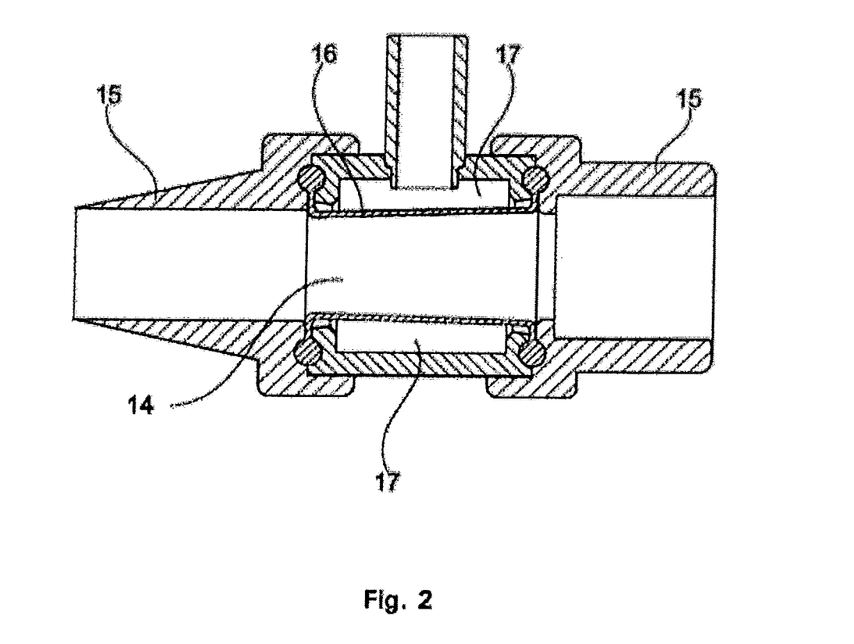
FIG. 2 shows a schematic longitudinal section as a diagram of a valve according to the invention in an open state.
Figure 3:
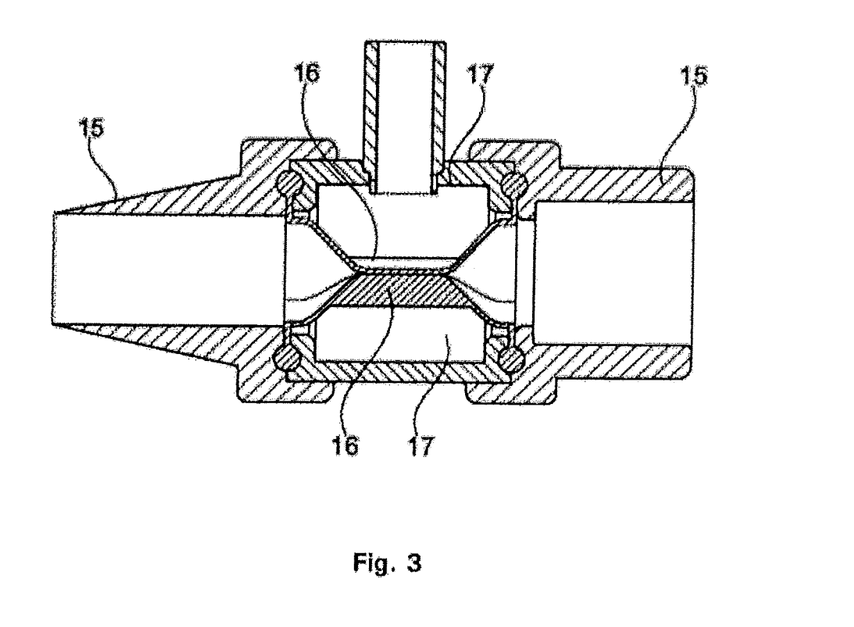
FIG. 3 shows a schematic longitudinal section as a diagram of a valve according to the invention in a closed state.
Figure 4:
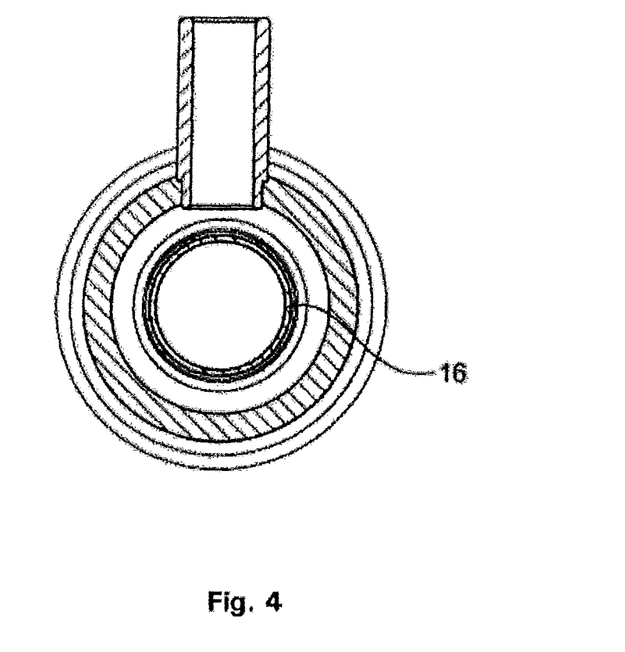
FIG. 4 shows a schematic cross-sectional diagram of a valve according to the invention in an open state.
Figure 5:
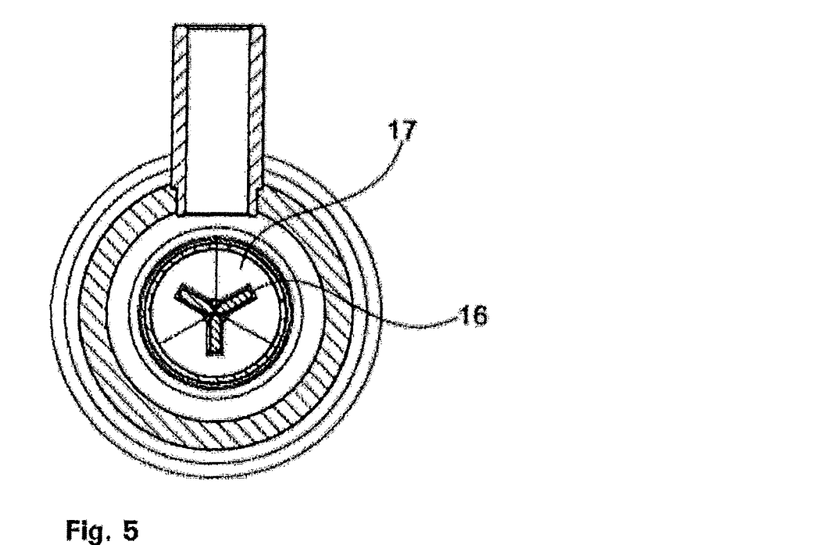
FIG. 5 shows a schematic cross-sectional diagram of a valve according to the invention in a closed state.

FIG. 2 shows the various components of a valve according to the invention in the open state of the valve: a channel 14, connecting elements 15, flexible wall segments 16, control chambers 17, which are interconnected to form a closed total volume system, which is acted upon by control fluid, wherein the flexible wall segments can be deformed reversibly as a function of the pressure of the control fluid applied in the control chambers. The flexible wall segments 146 are deformed in a jaw shape due to an increase in the pressure of the control fluid present in the control chamber 17 due to a movable piston which seals off the system, and the flexible wall segments are thereby squeezed into the cross of the channel and with respect to one another so that the powdered aerosol thereby produced is sealed off tightly (FIGS. 3 and 5). If the pressure of the control fluid present in the control chamber 17 is reduced, the flexible wall segments 16 open again to form a full passage (FIG. 4). In one application case for a premature infant of neonate, the total volume of the total volume system may amount to 0.7 mL. In this case, the valve may have an inside diameter of 5 mm and a length of 10 mm. In an application case for an adult, the total volume may amount to 14 mL. In this case, the valve may have an inside diameter of 19 mm and a length of 50 mm.

Figure 6:
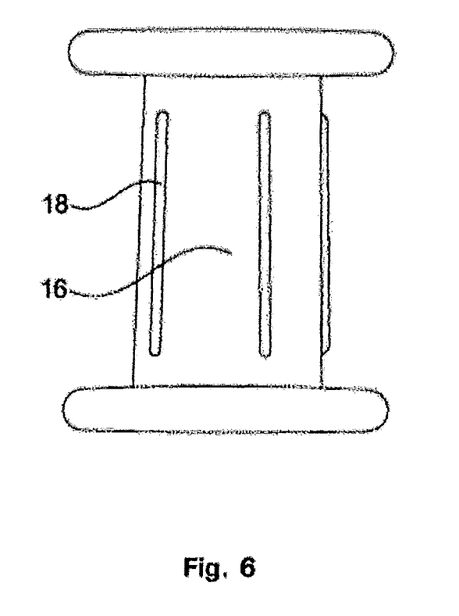
FIG. 6 shows a schematic diagram of one possible elastomer membrane-tubular cuff when the valve according to the invention is open.
Figure 7:
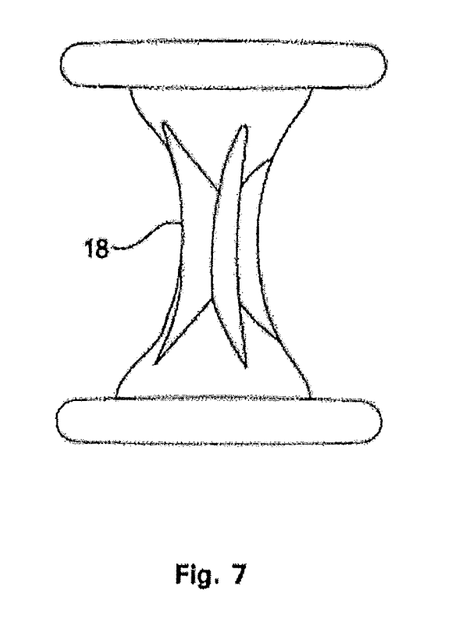
FIG. 7 shows a schematic diagram of one possible elastomer membrane-tubular cuff when the valve according to the invention is closed.

FIGS. 6 and 7 show a particularly advantageous embodiment of the closure elements as an elastomer membrane-tubular cuff which is arranged in the channel and both of whose ends are secured in a pressure-tight manner such that the elastomer membrane-tubular cuff has a plurality of reinforcements 18 along the length and distributed uniformly around the circumference, with the flexible wall segments 16 being formed between the reinforcements. In this way, in an implementation of the elastomer membrane-tubular cuff in the valve, the elastomer membrane-tubular cuff is deformed to a much lesser extent in comparison with the flexible wall segments 16 in the area of the reinforcements 18 due to an increase in the pressure of the control fluid present in the control chamber, the area between the reinforcements 18. The flexible wall segments 16 are deformed in the form of jaws and thereby squeezed into the cross section of the channel so that the line is tightly sealed.

Figure 8:
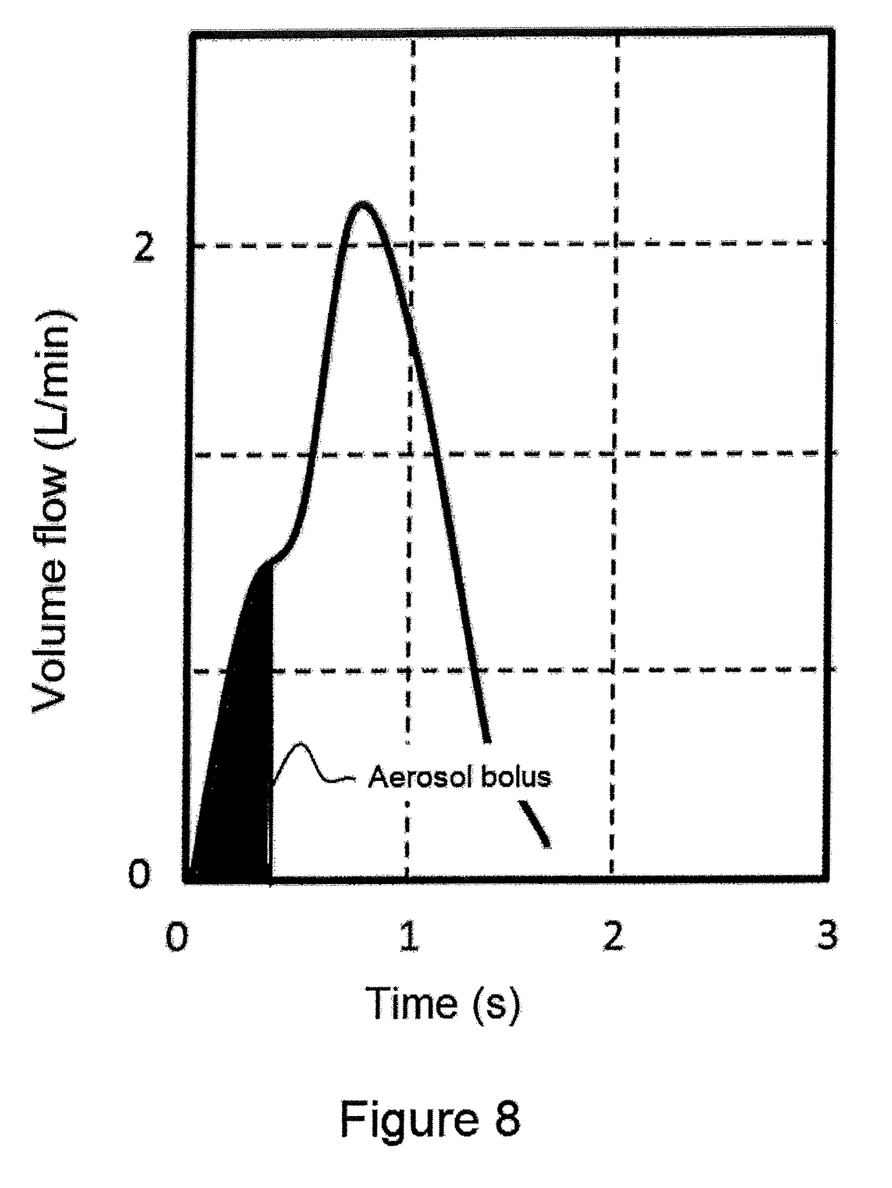
FIG. 8 shows an example of chronological placement of the powdered aerosol according to the present invention.

FIG. 8 shows as an example the chronological placement of the addition of active ingredient during an inhalation phase according to the present invention. The powdered aerosol here is added directly at the start of the inhalation phase, for example, so that the active ingredient can also reach the deep areas of the lungs. In this case, the duration and point in time of addition of an aerosol bolus can be adjusted through the valve. The added volume of powdered aerosol may amount to 20-30% of the patient's tidal volume.

LIST OF REFERENCE NUMERALS

1 Interface
2 Device for producing a respiratory gas stream
3 Inspiration line
4 Aerosol generator
5 Aerosol line
6 Respiration sensor
7 Valve
8 Temporary storage device
9 Controller
10 Expiration line
11 Filter
12 Moistener
13 Pressure sensor
14 Channel
15 Connecting elements
16 Flexible wall segments
17 Control chamber
18 Reinforcements

The invention claimed is:

1. A system for respiration-controlled administration of powdered aerosol in artificial respiration or supporting respiration of a patient, wherein the system comprises:
   an interface adapted to be brought into contact with a respiratory tract of the patient that is to receive the artificial respiration or the supporting respiration;
   a device for producing a respiratory gas stream, wherein the respiratory gas stream has a first pressure which is greater than or equal to an ambient pressure;
   at least one inspiration line through which the respiratory gas stream is sent to the interface;
   an aerosol generator that generates a powdered aerosol;
   at least one aerosol line through which the powdered aerosol is sent from the aerosol generator to the interface;
   a respiration sensor which detects a respiratory signal of the patient;
   a valve arranged in the at least one aerosol line between the interface and the aerosol generator, the valve being controlled as a function of the detected respiratory signal;
   a temporary storage device for storing powdered aerosol arranged between the valve and the aerosol generator; and
   a controller arranged to preset a second pressure which is greater than or equal to the first pressure and to cause the powdered aerosol to be generated in the aerosol generator and to be supplied to the temporary storage device until the pressure present in the temporary storage device corresponds to the second pressure preset by the controller;
   wherein the powdered aerosol stored in the temporary storage device is added directly to the respiratory gas stream based on the control of the valve.

2. The system according to claim 1, wherein the valve, when open, has an aperture corresponding to a cross section of the at least one aerosol line.

3. The system according to claim 1, wherein the valve has a switching time of less than 20 ms.

4. The system according to claim 1, wherein a line volume between the valve and the interface is less than a tidal volume of the patient.

5. The system according to claim 4, wherein the line volume between the valve and the interface amounts to a maximum of ¹⁄₁₀ of the patient's tidal volume.

6. The system according to claim 4, wherein a sum of a volume of the temporary storage device and of the line volume between the temporary storage device and the valve is greater than the patient's tidal volume.

7. The system according to claim 6, wherein the sum of the volume of the temporary storage device and of the line volume between the temporary storage device and the valve amounts to at least twice the patient's tidal volume.

8. The system according to any claim 1, wherein the temporary storage device has at least one elastic wall.

9. The system according to claim 1, wherein the aerosol generator is controlled as a function of the second pressure prevailing in the temporary storage device.

10. The system according to claim 1, wherein the valve includes a channel with connecting elements and a plurality of closure elements, wherein the plurality of closure elements have flexible wall segments and are arranged on an inside wall of the channel along a circumferential section in a radially uniform distribution so that the flexible wall segments each form control chambers with the inside wall of the channel, wherein the control chambers are interconnected with one another to form an overall volume system and are acted upon with a control fluid so that the plurality of closure elements is squeezed into a cross section of the channel and with respect to one another because of an increase in pressure of the control fluid in the control chambers.

11. The system according to claim 10, wherein a number of the plurality of closure elements is selected from the group consisting of three, four, and five identical closure elements in a radially symmetrical distribution, and wherein the volume of each the control chambers of the plurality of closure elements is the same.

12. The system according to claim 10 wherein a total volume of the system is maximum 1/3 of a tidal volume of the patient.

13. A method for respiration controlled administration of a powdered aerosol in artificial respiration or supporting respiration of a patient, comprising the following steps:
   generating a respiratory gas stream which has a first pressure greater than or equal to ambient pressure;
   sending the respiratory gas stream to an interface which is in contact with a respiratory tract of the patient to receive the artificial respiration or the supporting respiration;
   producing a powdered aerosol;
   sending the powdered aerosol to the interface;
   detecting a respiratory signal of the patient;
   storing the powdered aerosol in a temporary storage device located between a site of production of the powdered aerosol and the interface;
   controlling a preset second pressure which is greater than or equal to the first pressure by a controller;
   causing the generation of the powdered aerosol in the aerosol generator by the controller;
   supplying the powdered aerosol to the temporary storage device until a pressure present in the temporary storage device corresponds to the second pressure preset by the controller;
   wherein the powered aerosol stored in the temporary storage device is added directly to the respiratory gas stream based on the control of a valve; and
   regulating addition of the powdered aerosol by the valve as a function of the detected respiratory signal, where the valve is situated between the temporary storage device and the interface.

* * * * *